US009810907B2

(12) United States Patent  
Kitazawa et al.

(10) Patent No.: US 9,810,907 B2  
(45) Date of Patent: Nov. 7, 2017

(54) DISPLAY APPARATUS, DISPLAY METHOD, AND PROGRAM

(71) Applicant: Seiko Epson Corporation, Tokyo (JP)

(72) Inventors: Takayuki Kitazawa, Suwa (JP); Hideki Tanaka, Chino (JP); Yuya Maruyama, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/050,743

(22) Filed: Feb. 23, 2016

(65) Prior Publication Data

US 2016/0249008 A1   Aug. 25, 2016

(30) Foreign Application Priority Data

Feb. 24, 2015 (JP) ................................ 2015-033754

(51) Int. Cl.
| | | |
|---|---|---|
| H04N 5/77 | (2006.01) | |
| G02B 27/01 | (2006.01) | |
| G11B 27/031 | (2006.01) | |
| G06F 19/00 | (2011.01) | |

(52) U.S. Cl.  
CPC ....... *G02B 27/017* (2013.01); *G06F 19/3481* (2013.01); *G11B 27/031* (2013.01); *H04N 5/77* (2013.01)

(58) Field of Classification Search  
None  
See application file for complete search history.

(56) References Cited

U.S. PATENT DOCUMENTS

| | | | | |
|---|---|---|---|---|
| 2006/0257039 | A1* | 11/2006 | Matsuhira | .......... G06K 9/00241 382/254 |
| 2011/0019021 | A1* | 1/2011 | Yoshizumi | .......... H04N 5/2251 348/222.1 |
| 2014/0089980 | A1* | 3/2014 | Alexander | ......... H04N 5/44543 725/42 |
| 2014/0306866 | A1* | 10/2014 | Miller | ................... G06T 19/006 345/8 |

FOREIGN PATENT DOCUMENTS

| | | |
|---|---|---|
| JP | 2004-298430 A | 10/2004 |
| JP | 2007-020835 A | 2/2007 |

\* cited by examiner

*Primary Examiner* — Eileen Adams  
(74) *Attorney, Agent, or Firm* — Harness, Dickey & Pierce, P.L.C.

(57) ABSTRACT

A display apparatus includes a camera that outputs live motion images, a recorded motion image output section that outputs recorded motion images produced, a reversed motion image formation section that forms reversed motion images produced by reversing the live motion images, a skin color image extraction section that extracts images having a skin color from the live motion images and reverses the extracted images to form skin color reversed motion images, a motion image display section having a first display section and a second display section, and a display content setting section that sets display contents that are contents to be displayed in the first display section and the second display section, and the display content setting section selects contents to be displayed motion image display section from the live motion images, the recorded motion images, the reversed motion images, and the skin color reversed motion images.

17 Claims, 12 Drawing Sheets

DISPLAY APPARATUS, DISPLAY METHOD, AND PROGRAM

BACKGROUND

1. Technical Field

The present invention relates to a display apparatus, a display method, and a program.

2. Related Art

When the neural circuit in the brain is damaged due to a stroke, limbs are paralyzed in some cases. Methods that allow such a patient to undergo rehabilitation have been invented. One of the methods causes the patient to think that the patient should attempt moving a paralyzed limb and shows the patient images in which the paralyzed limb is moving so that the patient has a feeling as if the limb were moving.

A patient whose limb has been lost due, for example, to an accident sometimes has a painful sensation in the limb. The phenomenon is called a phantom pain. A method similar to the method described above has been proved to be effective for such a patient. In the method, an image that causes the patient to have a feeling as if the lost limb existed is shown to the patient. The method allows appropriate recognition of the lost limb in the brain of the patient to eliminate or alleviate the pain.

JP-A-2004-298430 discloses an apparatus that causes a patient to visually recognize as if a paralyzed hand or a lost hand were moving. According to JP-A-2004-298430, a plurality of magnetic sensors are attached to the body of the patient. A predetermined magnetic field is then applied to the patient, and the posture of the patient is detected. Motion images of the hand are then displayed on a display apparatus. In this process, the hand in the motion images is so adjusted in terms of position, posture, and size as to unite with the patient.

The patient who sees the motion images has a feeling as if the hand in the motion images were part of the body of the patient. The patient whose hand has been lost re-experiences a sense of unity of the hand in the brain, resulting in elimination or alleviation of the pain of the hand. In a case of a patient whose hand is paralyzed, the neural circuit is reconstructed in the brain, whereby the paralysis of the hand is alleviated.

In JP-A-2004-298430, the motion images to which the patient refers are images generated by an image generator. The images are animation images generated by a computer. Since the images are generated in real time, it is believed that the motion images are not formed of realistic images but are simplified images formed of polyhedrons. Further, JP-A-2004-298430 suggests that captured images are used, but it is believed in this case that the captured images are motion images that are not synchronized with the motion of the patient.

When a patient keeps conducting training, the neural circuit in the brain is reconstructed. It has been proved that for a patient who is not accustomed to training, motion images are preferably slowly displayed and a long standby period is preferably set when the action in the images changes. JP-A-2004-298430 suggests that the apparatus described therein has a mode in which animation images are used and a mode in which captured images are used. When animation images are used, they are images different from an actual body part and make it difficult for the patient to concentrate on training. Further, when the method does not fit the patient, the training is unlikely to be effective. As a method for conducting training, there is a training method that causes a patient to follow captured images as guidance to move a lost site or a paralyzed site. There is further an effective method that causes a patient to use a mirror and follow images showing motion of a normal body part as guidance. It has been desired to provide a display apparatus that allows a patient to efficiently conduct training by using a plurality of motion images that fit the patient's own training.

SUMMARY

An advantage of some aspects of the invention is to solve the problems described above, and the invention can be implemented as the following forms or application examples.

Application Example 1

A display apparatus according to this application example includes a live motion image output section that outputs live motion images, a recorded motion image output section that outputs recorded motion images, a reversed motion image formation section that reverses the live motion images to form reversed motion images, a skin color image extraction section that extracts images having a skin color from the live motion images and reverses the extracted images to form skin color reversed motion images, a motion image display section having a first display section and a second display section, and a display content setting section that sets display contents that are contents to be displayed in the first display section and the second display section, and the live motion images, the recorded motion images, the reversed motion images, and the skin color reversed motion images are settable as the display contents.

According to this application example, the display apparatus includes the motion image display section, and the motion image display section includes the first display section and the second display section. Each of the first display section and the second display section displays motion images. The display apparatus further includes an imaging section, the recorded motion image output section, the reversed motion image formation section, the skin color image extraction section, and the display content setting section. The imaging section outputs live motion images produced by capturing images of a body part to the motion image display section. The recorded motion image output section outputs recorded motion images to the motion image display section. The reversed motion image formation section outputs reversed motion images produced by reversing the live motion images to the motion image display section. The skin color image extraction section outputs skin color reversed motion images produced by extracting images having a skin color from the live motion images and reversing the extracted images to the motion image display section.

The display content setting section can set display contents that are contents to be displayed in the first display section and the second display section. Stroke-related training and phantom-pain-related training can therefore be conducted by setting the display contents in the first display section and the second display section in accordance with the content of the training. A patient can select one of the live motion images, the recorded motion images, the reversed motion images, and the skin color reversed motion images as motion images that allow the patient to readily conduct training. The patient can therefore select a combination of motion images that fits the patient's own training and display the combination in the first display section and the second display section, whereby the training can be efficiently conducted.

Application Example 2

In the display apparatus according to the application example described above, the display content setting section causes a setting screen that prompts input of the display contents to be displayed, and the setting screen, which is formed of a single setting screen, allows both the display content in the first display section and the display content in the second display section to be set.

According to this application example, the display content setting section displays a setting screen that prompts input of the display contents. Both the display content in the first display section and the display content in the second display section can be set in the single display screen. The display contents can therefore be set in the first display section and in the second display section without switching the setting screen, whereby the display contents in the motion image display section can be readily set.

Application Example 3

In the display apparatus according to the application example described above, the live motion images are displayed in one of the first display section and the second display section, and the recorded motion images are displayed in the other.

According to this application example, the motion image display section displays recorded motion images and live motion images. The patient can conduct stroke-related training by using the display apparatus. The patient moves a paralyzed body part by following the recorded motion images as guidance. The patient can conduct the training while checking the motion of the body part by viewing the live motion images. Since the patient can conduct the training while checking an effect of the training, the training can be efficiently conducted.

Application Example 4

In the display apparatus according to the application example described above, the motion image display section is a light-transmissive head-mounted display, and when no motion images are displayed in the first display section or the second display section, a scene having passed through the motion image display section is visible.

According to this application example, the motion image display section is a light-transmissive head-mounted display. When no display is made in the first display section, the first display section becomes light transmissive, whereby the patient can view the patient's own body part through the first display section. Similarly, when no display is made in the second display section, the second display section becomes light transmissive, whereby the patient can view the patient's own body part through the second display section. The patient can therefore readily check the motion of the patient's own body part.

Application Example 5

A display apparatus according to this application example includes a motion image display section having a first display section and a second display section, and live motion images are displayed in one of the first display section and the second display section, and motion images different from the live motion images are displayed in the other.

According to this application example, the display apparatus includes an imaging section, a live motion image output section, a recorded motion image output section, and the motion image display section. A patient conducts stroke-related training and other types of training by using the display apparatus. The motion image display section displays live motion images and motion images. The patient moves a paralyzed body part by following the motion images as guidance. The patient conducts the training while checking the motion of the body part by checking the motion of the body part by viewing the live motion images. Therefore, since the patient can simultaneously view the guidance and the action of the patient's own body part, the training can be efficiently conducted.

Application Example 6

In the display apparatus according to the application example described above, the motion images are recorded motion images produced by capturing images of guidance action.

According to this application example, the motion images are recorded motion images produced by capturing images of guidance action. The patient can therefore conduct the training by using motion images that have recorded action that the patient can readily follow. As a result, the patient can efficiently conduct the training.

Application Example 7

In the display apparatus according to the application example described above, the motion images are reversed motion images produced by reversing the live motion images.

According to this application example, the motion images are reversed motion images produced by reversing the live motion images. The reversed motion images are motion images produced by reversing motion images of the action of a normal body part of the patient. The patient therefore manipulates action guidance by himself/herself, whereby the patient can conduct the training by using motion images showing action that the patient can readily follow. As a result, the patient can efficiently conduct the training.

Application Example 8

In the display apparatus according to the application example described above, the motion images are skin color reversed motion images produced by extracting images having a skin color from the live motion images and reversing the extracted images.

According to this application example, the motion images are skin color reversed motion images. Since the background image in the skin color reversed motion images is removed, the patient can concentrate on the motion of the body part.

Application Example 9

A display method according to this application example includes displaying motion images in a first display section and a second display section by using one of the following combinations: a first combination in which recorded motion images are displayed in the first display section and live motion images are displayed in the second display section;

a second combination in which the live motion images are displayed in the first display section and reversed motion images produced by reversing the live motion images are displayed in the second display section; and a third combination in which recorded motion images are displayed in the first display section and the second display section.

According to this application example, one of the first combination, the second combination, and the third combination is selected, and training is so conducted that a patient moves part of a body part while viewing the first display section and the second display section. The first combination allows stroke-related training to be conducted. The first display section displays recorded motion images, and the second display section displays live motion images of the part of the body part. The patient can check the motion of the part of the body part while moving the part of the body part by following the recorded motion images as guidance. Therefore, since the patient can simultaneously view the guidance and the action of the patient's own body part, the training can be efficiently conducted.

The second combination allows phantom-pain-related training to be conducted. The first display section displays live motion images of part of a body part, and the second display section displays reversed motion images produced by reversing live motion images of the part of the body part. The patient conjures action of moving a lost body part in his/her mind while viewing the live motion images and the reversed motion images. The patient moves the normal body part in such a way that the patient readily conjures the action in his/her mind. Since the patient conducts training that the patient conjures in his/her mind when viewing the reversed motion images of the action, the patient can concentrate on the reversed motion images in the training. As a result, the training can be efficiently conducted.

The third combination allows phantom-pain-related practice to be conducted. The first display section and the second display section display recorded motion images. The patient conjures action of moving lost body parts in his/her mind while viewing the recorded motion images. In this process, since the patient can concentrate on the motion of the body parts shown in the recorded motion images, the training can be efficiently conducted. Since the patient can select one of the first, second, and third combinations, a patient having a plurality of conditions can use a single apparatus for efficient training.

Application Example 10

In the display method according to the application example described above, in the second combination, skin color reversed motion images produced by extracting images having a skin color from the live motion images and reversing the extracted images are displayed in the second display section.

According to this application example, the second display section displays skin color reversed motion images. Since the background image is removed in the skin color reversed motion images, the patient can concentrate on the motion of a body part in the training.

Application Example 11

A program according to this application example is a program that causes a computer to function as a live motion image output functional section that outputs live motion images, a recorded motion image output functional section that outputs recorded motion images, a reversed motion image formation functional section that reverses the live motion images to form reversed motion images, a skin color image extraction functional section that extracts images having a skin color from the live motion images and reverses the extracted images to form skin color reversed motion images, and a display content setting functional section that sets display contents that are contents to be displayed in a first display section and a second display section, and the live motion images, the recorded motion images, the reversed motion images, and the skin color reversed motion images are settable as the display contents.

According to this application example, the program causes a computer to function as a live motion image output functional section that outputs live motion images, a recorded motion image output functional section that outputs recorded motion images, a reversed motion image formation functional section that reverses the live motion images to form reversed motion images, a skin color image extraction functional section that extracts images having a skin color from the live motion images and reverses the extracted images to form skin color reversed motion images, and a display content setting functional section that sets display contents that are contents to be displayed in a first display section and a second display section. Stroke-related training and phantom-pain-related training can therefore be conducted by allowing the display contents to be set in the first display section and the second display section in accordance with the content of the training. A patient can select one of the live motion images, the recorded motion images, the reversed motion images, and the skin color reversed motion images as motion images that allow the patient to readily conduct training. The patient can therefore select a combination of motion images that fits the patient's own training, whereby the training can be efficiently conducted.

Application Example 12

A display apparatus according to this application example includes a recorded motion image output section that outputs recorded motion images produced by recording motion images and a light-transmissive head-mounted display having a first display section and a second display section, and the recorded motion images are displayed in one of the first display section and the second display section.

According to this application example, the display apparatus includes a recorded motion image output section and a light-transmissive head-mounted display. Recorded motion images are displayed in one of the first display section and the second display section. The other display section allows a patient to view a body part of the patient through a motion image display section. The patient can therefore move a paralyzed body part by following the recorded motion images as guidance and check the motion of the paralyzed body part. Therefore, since the patient can simultaneously view the guidance and the action of the patient's own body part, the patient can conduct the training while checking an effect of the training. As a result, the training can be efficiently conducted.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
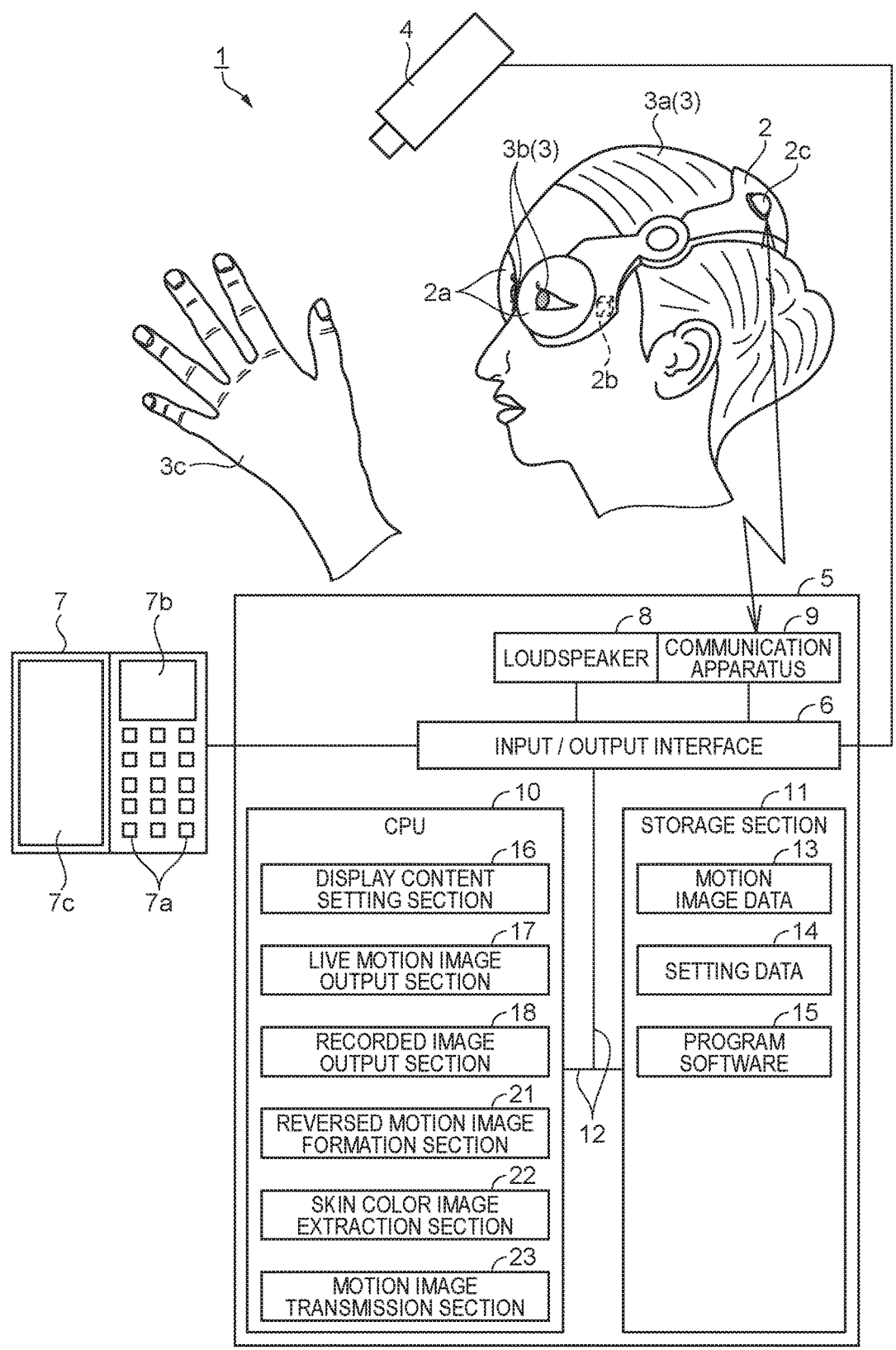
FIG. 1 is a block diagram showing the configuration of a rehabilitation assistance apparatus according to a first embodiment.

In embodiments of the invention, characteristic examples of a rehabilitation assistance apparatus and a method for performing rehabilitation therapy by using the rehabilitation assistance apparatus will be described with reference to figures. The embodiments will be described below with reference to the drawings. Each member in the drawings is so drawn at different scales as to be large enough to be recognizable in the drawings.

First Embodiment

A rehabilitation assistance apparatus according to a first embodiment will be described with reference to FIGS. 1 and 2. FIG. 1 is a block diagram showing the configuration of the rehabilitation assistance apparatus. A rehabilitation assistance apparatus 1 as a display apparatus includes a head-mounted display 2 as a motion image display section and a light transmissive head-mounted display, and the head-mounted display 2 is mounted on a head 3a of a patient 3, as shown in FIG. 1. The head-mounted display 2 has mirror sections 2a so located as to face eyes 3b of the patient 3. The head-mounted display 2 includes projection sections 2b, and the projection sections 2b output light toward the mirror sections 2a. The light is reflected off the mirror sections 2a and incident on the eyes 3b. The patient 3 can view virtual motion images on the basis of the light incident on the eyes 3b. The head-mounted display 2 allows the right eye and the left eye to see motion images different from each other. The head-mounted display 2 therefore allows the patient 3 to view not only a planar screen image but also a stereoscopic virtual image.

Each of the mirror sections 2a is a transmissive mirror, and the head-mounted display 2 is therefore referred to as a light-transmissive head-mounted display. When the projection sections 2b output no light, the patient 3 can view an external image that is a scene in front of the patient 3 through the mirror sections 2a. When the projection sections 2b output light, the patient 3 sees an image projected by the projection sections 2b and superimposed on the scene in front of the patient 3.

The rehabilitation assistance apparatus 1 includes a camera 4 as an imaging section. The camera 4 is capable of high-speed imaging and can capture 300 screen images per second. The camera 4 has an objective lens and a CCD (charge coupled device) imaging element incorporated therein. The objective lens provided in the camera 4 has a large depth of focus. Light reflected off an object within view of the patient 3 is inputted to the camera 4 through the objective lens, and the light having passed through the objective lens forms an image on the CCD imaging element. The CCD imaging element converts the image formed thereon into an electrical signal. Images of the object within view of the patient 3 can thus be captured. The camera 4 can be formed of an imaging tube or a CMOS (complementary metal oxide semiconductor) imaging sensor in place of the CCD imaging element. The camera 4 may instead be formed of an infrared image sensor.

The head-mounted display 2 includes a communication section 2c. The rehabilitation assistance apparatus 1 includes a control apparatus 5 as a computer, and the communication section 2c communicates with the control apparatus 5 and transmits and receives data to and from the control apparatus 5. The communication section 2c may perform communication by using a radio wave as a communication medium or wireless or wired communication, such as communication using light as a communication medium. In the present embodiment, the communication section 2c is, for example, an apparatus that performs Bluetooth communication.

The patient 3 has hands 3c as a body part. One of the hands 3c of the patient 3 has been lost or is paralyzed, and the other hand 3c is in good shape. The patient 3 uses the rehabilitation assistance apparatus 1 to conduct training that allows removal of an itch and pain that the patient 3 feels in the lost hand 3c. The patient 3 instead uses the rehabilitation assistance apparatus 1 to conduct training in such a way that the patient 3 can move the paralyzed hand 3c. The camera 4 outputs captured images that are images of the hand 3c captured with the camera 4 (live motion images) to the communication section 2c. The communication section 2c transmits data on the captured images to the control apparatus 5.

The control apparatus 5 includes an input/output interface 6, to which an input/output terminal 7 as a display content setting section, a loudspeaker 8, and a communication apparatus 9 are connected. The input/output terminal 7 has input keys 7a, a touch panel 7b, and a display section 7c. The input keys 7a are buttons with which the patient 3 inputs an instruction content when the patient 3 operates the rehabilitation assistance apparatus 1. The touch panel 7b is a portion where the patient 3 manipulates a pointer in an image displayed on the head-mounted display 2 and the display section 7c. The patient 3 can move the pointer by touching the surface of the touch panel 7b with a finger and moving the finger. Further, the patient 3 can issue an instruction to select the position where the pointer is located by lightly tapping the surface of the touch panel 7b. The touch panel 7b can be formed, for example, of a capacitance sensor or a pressure sensor.

The head-mounted display 2 mounted on the patient 3 makes it difficult for the patient 3 to see the input keys 7a. In this case, the patient 3 can operate the rehabilitation assistance apparatus 1 by operating the touch panel 7b in a groping-around manner to operate the in-screen pointer displayed on the head-mounted display 2. The display section 7c displays the same motion images or images as those displayed on the head-mounted display 2. An assistant who assists the patient 3 in conduct training can view motion images on the display section 7c and guide the patient 3. Further, the assistant can operate the input keys 7a and the tough panel 7b to operate the rehabilitation assistance apparatus 1.

The loudspeaker 8 has a function of conveying a message to the patient 3 in the form of a voice signal. When the patient 3 is conducting rehabilitation training, but when the patient 3 is not focusing his/her attention on motion images displayed on the mirror sections 2a, the control apparatus 5 can convey a message to the patient 3 via the loudspeaker 8.

The communication apparatus 9 is an apparatus that communicates with the communication section 2c incorporated in the head-mounted display 2. The communication apparatus 9 and the communication section 2c send and receive data on motion images outputted from the projection sections 2b and other kinds of data to and from each other.

The control apparatus 5 further includes a CPU 10 (central processing unit), which serves as a computation section that performs a variety of types of computation as a processor, and a storage section 11, which stores a variety of types of information. The input/output interface 6 and the storage section 11 are connected to the CPU 10 via a data bus 12.

The storage section 11 is a concept including a RAM, a ROM, and other semiconductor memories and a hard disk drive, a DVD-ROM, and other external storage devices. From a functional viewpoint, a storage region for storing motion image data 13 projected by the projection sections 2b is set. The motion image data 13 includes data on motion images captured with the camera 4 and data on motion images processed by the CPU 10. Further, a storage region for storing setting data 14, which is data on display contents that are contents displayed by the head-mounted display 2, is also set. Still further, a storage region for storing program software 15 as a program that describes control procedure in accordance with which the rehabilitation assistance apparatus 1 operates is also set. Still further, a storage region that functions, for example, as a work area and a temporary file used by the CPU 10 and a variety of other storage regions are set.

The CPU 10 controls the rehabilitation assistance apparatus 1 in accordance with the program software 15 stored in the storage section 11. As specific, function-realizing sections, the CPU 10 includes a display content setting section 16 as a display content setting functional section, a live motion image output section 17 as a live motion image output functional section, a recorded motion image output section 18 as a recorded motion image output section and a recorded motion image output functional section, a reversed motion image formation section 21 as a reversed motion image formation functional section, a skin color image extraction section 22 as a skin color image extraction functional section, a motion image transmission section 23 as a motion image output section, and other sections. The display content setting section 16 sets display contents to be displayed on the head-mounted display 2. The display content setting section 16 displays a screen that prompts input of display contents to be displayed on the head-mounted display 2 and the display section 7c. The patient 3 or the assistant then operates the input keys 7a or the touch panel 7b to input display contents. The display content setting section 16 then stores the display contents as the setting data 14 in the storage section 11.

The CPU 10 further includes the live motion image output section 17. The live motion image output section 17 stores live motion images captured with the camera 4 as the motion image data 13 in the storage section 11. The live motion images are motion images produced by capturing images of action of the hand 3c. Further, the live motion image output section 17 outputs the live motion images to the reversed motion image formation section 21, the skin color image extraction section 22, and the motion image transmission section 23. The CPU 10 further includes the recorded motion image output section 18. The recorded motion image output section 18 outputs recorded motion images, which are motion images having been recorded before and stored as the motion image data 13 in the storage section 11, to the motion image transmission section 23. The CPU 10 can therefore output recorded motion images in which the hand 3c in good shape normally moves.

The CPU 10 further includes the reversed motion image formation section 21. The reversed motion image formation section 21 forms reversed motion images produced by reversing live motion images in which the hand 3c in good shape normally moves. When the live motion images are motion images of the right hand, the reversed motion images are motion images shown as if the left hand were moving. When the live motion images are motion images of the left hand, the reversed motion images are motion images shown as if the right hand were moving. The reversed motion image formation section 21 then stores the reversed motion images as the motion image data 13 in the storage section 11 and outputs the reversed motion images to the motion image transmission section 23.

The CPU 10 further includes the skin color image extraction section 22. The skin color image extraction section 22 extracts a skin color portion formed of the hand 3c from the live motion images. The skin color image extraction section 22 further forms skin color reversed motion images produced by reversing the extracted images of the hand 3c. In the skin color reversed motion images, images of the hand 3c are displayed, but the background displayed in the live motion images is removed. In the skin color reversed motion images, the portion other than the images of the hand 3c is a black background, that is, a region toward which the projection sections 2b output no light. Since the head-mounted display 2 is a light transmissive display, the black portion of the skin color reversed motion images allows the patient 3 to see an external background through the mirror sections 2a. When the patient 3 sees the skin color reversed motion images, the images of the hand 3c are so displayed as to be superimposed on the external background viewed through the mirror sections 2a. The skin color image extraction section 22 stores the skin color reversed motion images as the motion image data 13 and outputs images to the motion image transmission section 23.

The CPU 10 further includes the motion image transmission section 23. The motion image transmission section 23 has a function of transferring the live motion images, the recorded motion images, the reversed motion images, and the skin color reversed motion images, which are stored as the motion image data 13, to the head-mounted display 2 and the display section 7c. The head-mounted display 2 includes a memory that stores data on motion images. The motion image transmission section 23 transfers data on the motion images to the memory in the head-mounted display 2. In the head-mounted display 2, the projection sections 2b use the motion image data transferred to the memory to project the motion images.

Figure 2:
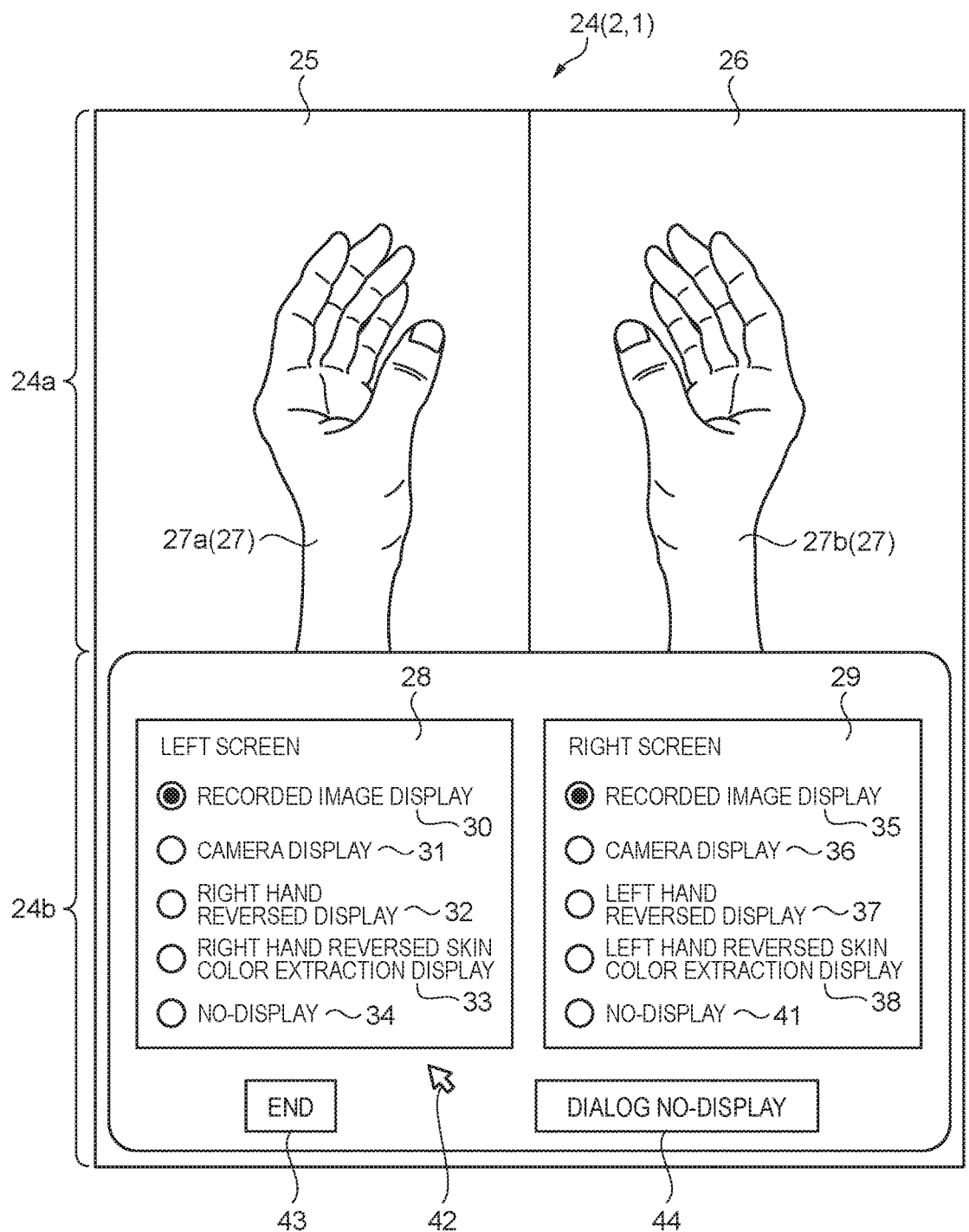
FIG. 2 is a diagrammatic view for describing a display screen.

FIG. 2 is a diagrammatic view for describing a display screen. A display screen 24 as a motion image display section shown in FIG. 2 is a screen displayed on the head-mounted display 2 and the display section 7c. The display screen 24 is formed of an image section 24a and a dialog section 24b, the latter of which serves as a setting screen. The image section 24a displays the live motion images, the recorded motion images, the reversed motion images, and the skin color reversed motion images. When the image section 24a displays no motion images, the patient 3 sees an external background through the mirror sections 2a.

The image section 24a is formed of a first display section 25 and a second display section 26. The first display section 25 and the second display section 26 are disposed side by side, and the patient 3 conducts training while simultaneously viewing the first display section 25 and the second display section 26. The first display section 25 displays left hand images 27a or the left hand of the patient 3. The second display section 26 displays right hand images 27b or the right hand of the patient 3. The present embodiment is an embodiment in which the patient 3 who has lost one of the hands 3c or the patient 3 who has one paralyzed hand 3c conducts training. The recorded motion images, the reversed motion images, and the skin color reversed motion images are motion images formed of hand images 27 in which the following transitions are repeated: a transition from a state in which the patient 3 clenches his/her hand to a state in which the patient 3 unclenches his/her hand and transition from the state in which the patient 3 unclenches his/her hand to the state in which the patient 3 clenches his/her hand.

The dialog section 24b is a screen for setting display contents that the patient 3 or the assistant desires to display in the image section 24a. The display content setting section 16 displays the dialog section 24b to prompt the patient 3 or the assistant to input setting contents. In an upper portion of the depicted dialog section 24b, a first input section 28 and a second input section 29 are set. The first input section 28 is a screen for setting the display content in the first display section 25, and the second input section 29 is a screen for setting the display content in the second display section 26. Since the first input section 28 and the second input section 29 are displayed in one screen, the display content in the first display section 25 and the display content in the second display section 26 can be set without switching a screen to another. Items set in the first input section 28 and items set in the second input section 29 are roughly identical. Setting items in the first input section 28 will first be described.

A recorded image display selecting section 30 is set in an upper portion of the depicted first input section 28. When the recorded image display selecting section 30 is selected, the recorded motion image output section 18 outputs the recorded motion images stored as the motion image data 13 in the storage section 11 to the motion image transmission section 23. The motion image transmission section 23 transmits data on the recorded motion images to the head-mounted display 2. The head-mounted display 2 receives the data on the recorded motion images and displays the recorded motion images in the first display section 25. The first display section 25 then displays the recorded motion images. The recorded motion images are motion images formed of moving left hand images 27a.

A camera display selecting section 31 is set below the depicted recorded image display selecting section 30. When the camera display selecting section 31 is selected, the live motion image output section 17 outputs data on the live motion images captured with the camera 4 to the communication apparatus 9. The communication apparatus 9 transmits the data on the live motion images to the head-mounted display 2. The head-mounted display 2 receives the data on the live motion images and displays the live motion images in the first display section 25.

A right hand reversed display selecting section 32 is set below the depicted camera display selecting section 31. When the right hand reversed display selecting section 32 is selected, the reversed motion image formation section 21 forms reversed motion images produced by reversing the live motion images. The reversed motion image formation section 21 then outputs the reversed motion images to the communication apparatus 9. The communication apparatus 9 transmits data on the reversed motion images to the head-mounted display 2. The head-mounted display 2 receives the data on the reversed motion images and displays the reversed motion images in the first display section 25. The reversed motion images displayed in the first display section 25 are motion images formed of images produced by reversing the right hand images 27b, which are captured right hand images.

A right hand reversed skin color extraction display selecting section 33 is set below the depicted right hand reversed display selecting section 32. When the right hand reversed skin color extraction display selecting section 33 is selected, the skin color image extraction section 22 extracts images having the skin color from the live motion images and reverses the extracted images to form skin color reversed motion images. The skin color image extraction section 22 then outputs the skin color reversed motion images to the communication apparatus 9. The communication apparatus 9 transmits data on the skin color reversed motion images to the head-mounted display 2. The head-mounted display 2 receives the data on the skin color reversed motion images and displays the skin color reversed motion images in the first display section 25. The skin color reversed motion images displayed in the first display section 25 are motion images formed of images produced by extracting the right hand images 27b, which are captured right hand images, and reversing the extracted right hand images 27b. The background of the skin color reversed motion images has been removed.

A no-display selecting section 34 is set below the depicted right hand reversed skin color extraction display selecting section 33. When the no-display selecting section 34 is selected, no motion images are displayed in the first display section 25, and the patient 3 is therefore allowed to see an external background through the mirror sections 2a. Setting items in the second input section 29 will next be described.

A recorded image display selecting section 35 is set in an upper portion of the depicted second input section 29. When the recorded image display selecting section 35 is selected, recorded motion images are displayed in the second display section 26. The recorded motion images are motion images formed of moving right hand images 27b. A camera display selecting section 36 is set below the depicted recorded image display selecting section 35. When the camera display selecting section 36 is selected, live motion images are displayed in the second display section 26.

A left hand reversed display selecting section 37 is set below the depicted camera display selecting section 36. When the left hand reversed display selecting section 37 is selected, reversed motion images are displayed in the second display section 26. The reversed motion images displayed in the second display section 26 are motion images formed of images produced by reversing the left hand images 27a, which are captured left hand images.

A left hand reversed skin color extraction display selecting section 38 is set below the depicted left hand reversed display selecting section 37. When the left hand reversed skin color extraction display selecting section 38 is selected, skin color reversed motion images are displayed in the second display section 26. The skin color reversed motion images displayed in the second display section 26 are motion images formed of images produced by extracting the left hand images 27a from captured left hand motion images and reversing the extracted left hand images 27a. The background of the skin color reversed motion images has been removed.

A no-display selecting section 41 is set below the depicted left hand reversed skin color extraction display selecting section 38. When the no-display selecting section 41 is selected, no motion images are displayed in the second display section 26, and the patient 3 is therefore allowed to see an external background through the mirror sections 2a.

A pointer 42 is displayed in the dialog section 24b. The pointer 42 is a mark having an arrow shape. The patient 3 and the assistant can move the pointer 42 by touching the touch panel 7b with a finger and moving the finger. When the pointer 42 is moved to any of open circular marks drawn at the recorded image display selecting section 30 to the no-display selecting section 41, and the touch panel 7b is lightly tapped with a finger, the item pointed with the pointer 42 is selected. A filled circular mark is then drawn at the center of the open circular mark to visually show the selected item.

In the first input section 28, only one of the recorded image display selecting section 30 to the no-display selecting section 34 can be selected. For example, in a state in which the recorded image display selecting section 30 has been selected, selecting the camera display selecting section 31 causes the filled circular mark to move from the recorded image display selecting section 30 to the camera display selecting section 31. Similarly, in the second input section 29, only one of the recorded image display selecting section 35 to the no-display selecting section 41 can be selected.

An end mark 43 is set in a lower portion of the depicted first input section 28. When the patient 3 or the assistant move the pointer 42 to the end mark 43 and lightly tap the touch panel 7b with a finger, the rehabilitation assistance apparatus 1 stops operating. A dialog no-display mark 44 is set in a lower portion of the depicted second input section 29. When the pointer 42 is moved to the dialog no-display mark 44, and the touch panel 7b is lightly tapped with a finger, the displayed dialog section 24b is removed so that the area of the image section 24a can be enlarged. The rehabilitation assistance apparatus 1 can be restarted and the dialog section 24b can be redisplayed by operation of corresponding ones of the input keys 7a.

Figure 3:
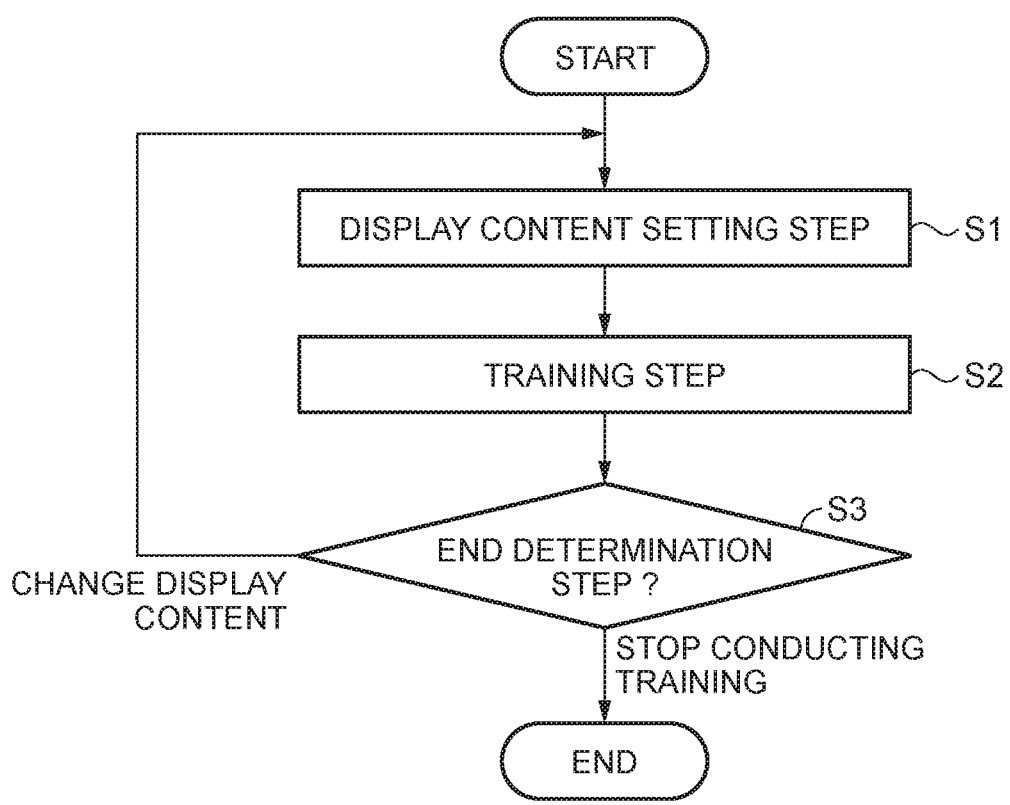
FIG. 3 is a flowchart of a rehabilitation method.
Figure 4:
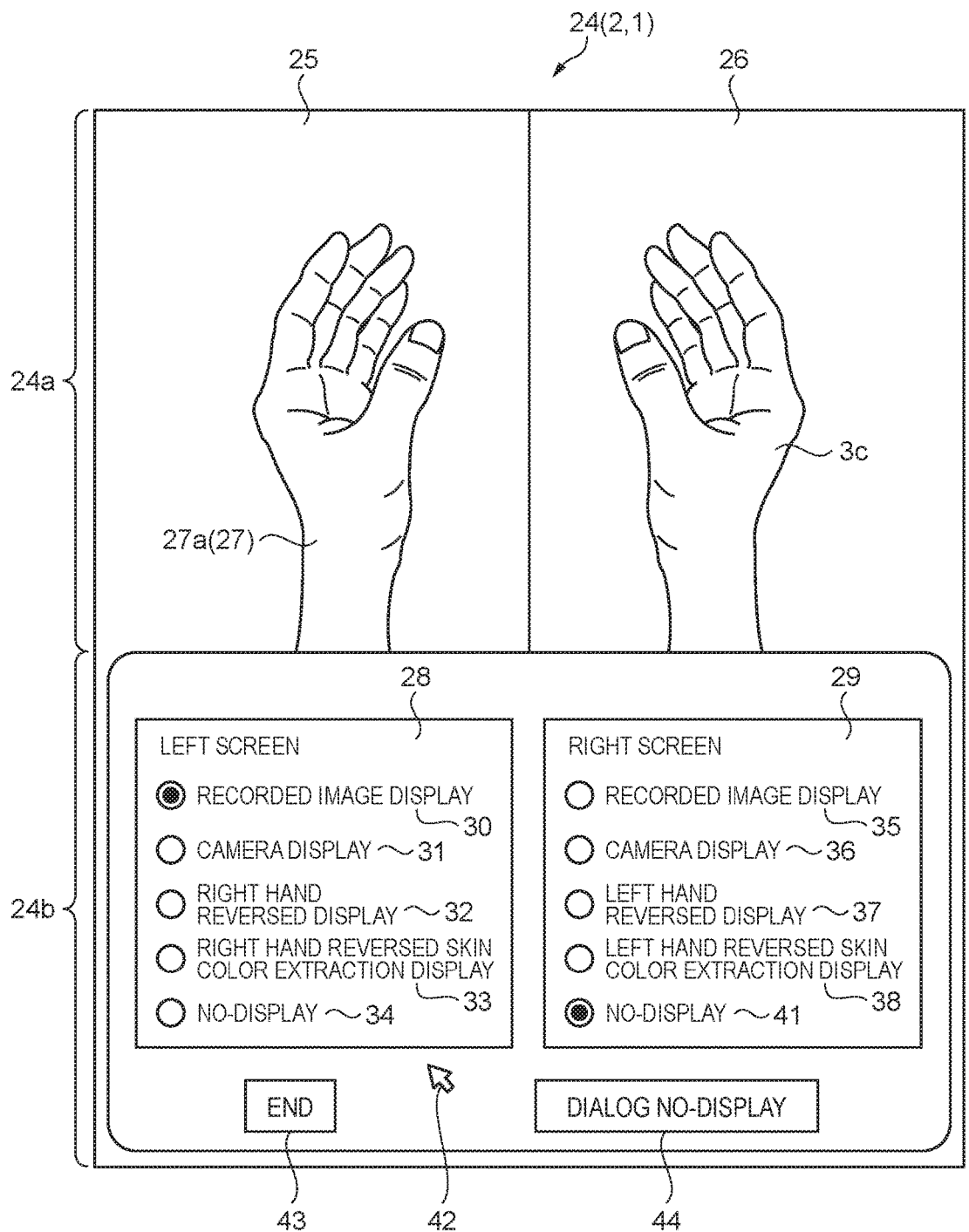
FIG. 4 is a diagrammatic view for describing the rehabilitation method.
Figure 5:
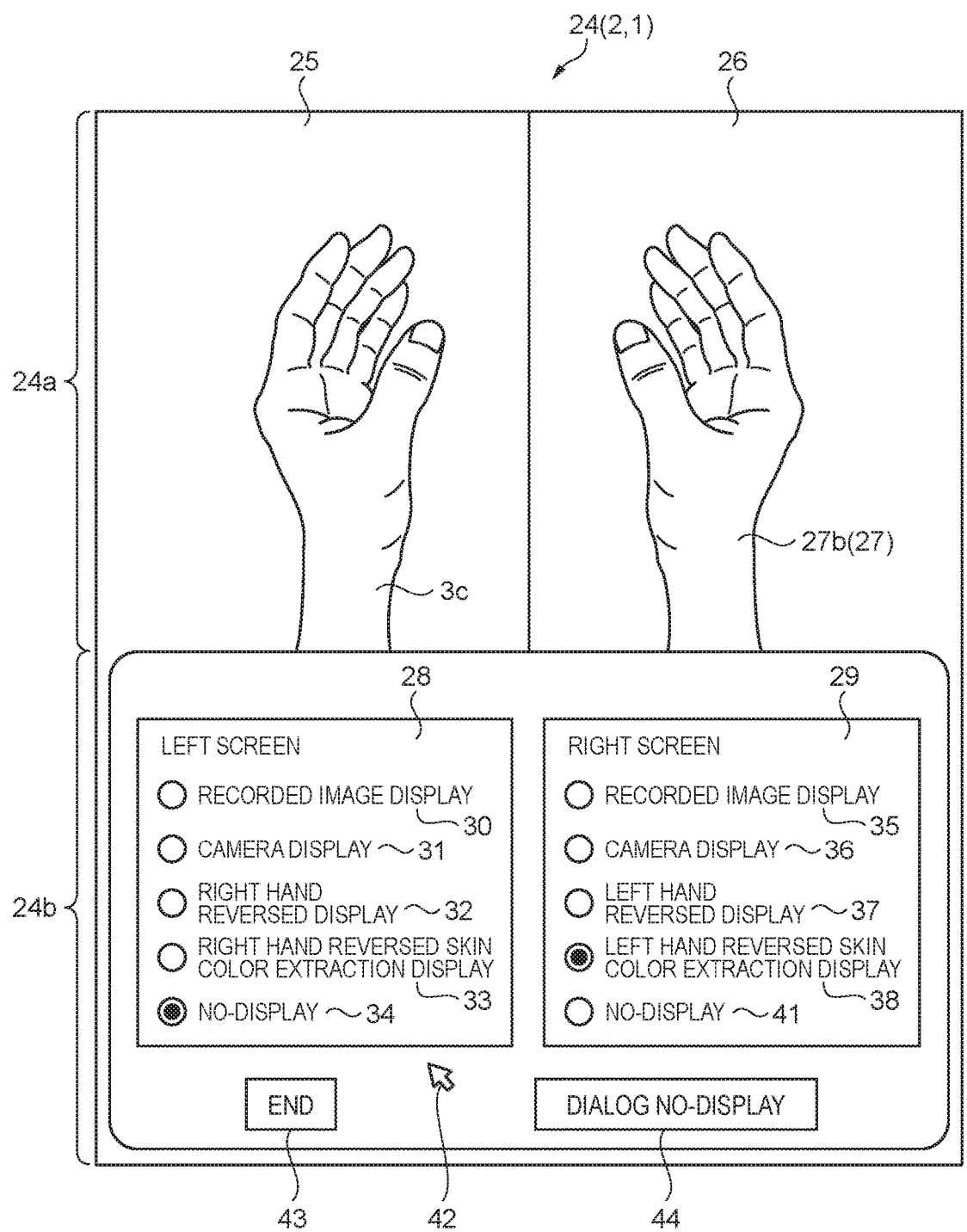
FIG. 5 is another diagrammatic view for describing the rehabilitation method.
Figure 6:
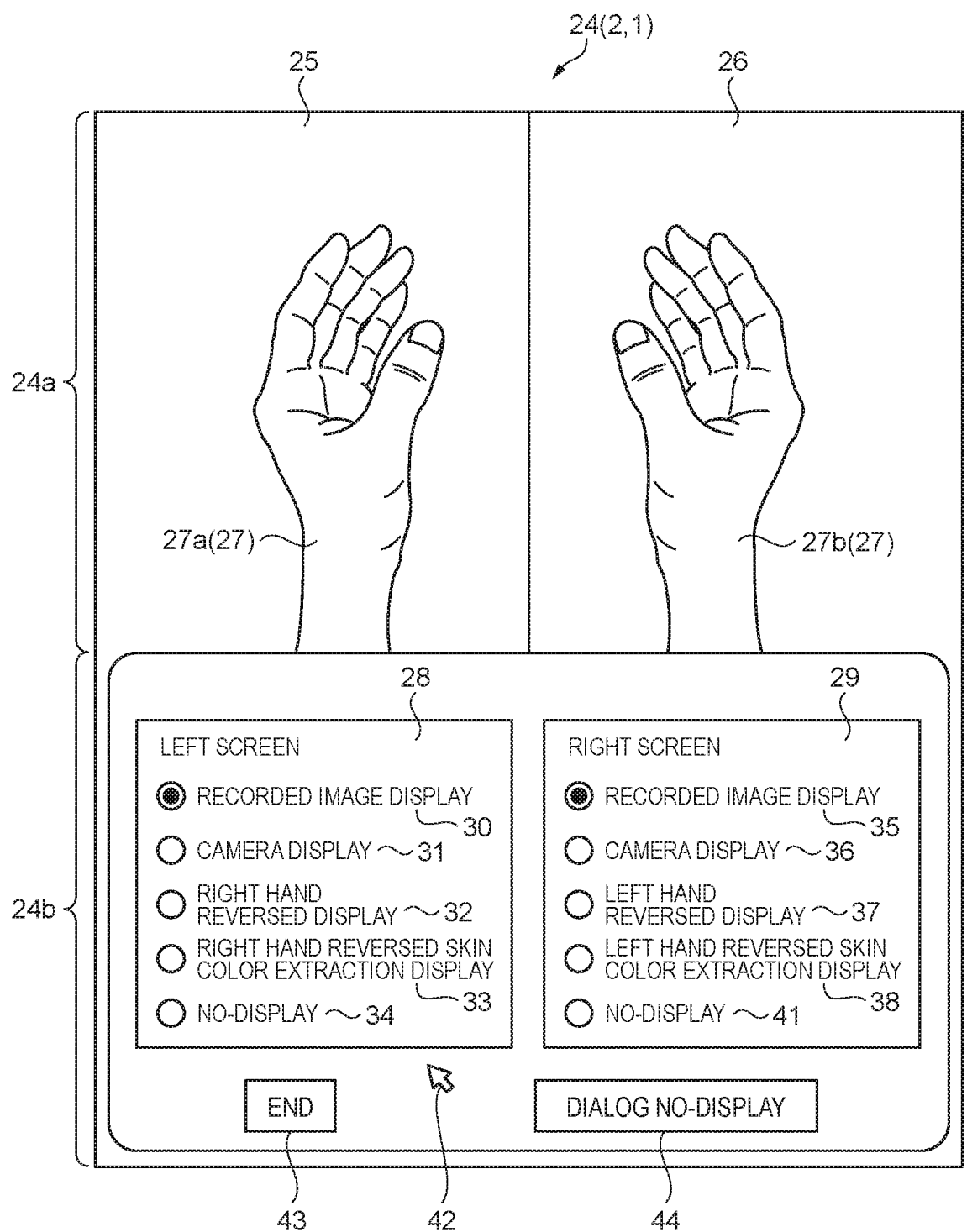
FIG. 6 is another diagrammatic view for describing the rehabilitation method.

A phantom pain treatment method using the rehabilitation assistance apparatus 1 described above will next be described with reference to FIGS. 3 to 6. FIG. 3 is a flowchart of the rehabilitation method. FIGS. 4 to 6 are diagrammatic views for describing the rehabilitation method. In the flowchart shown in FIG. 3, step S1 corresponds to a display content setting step, which is the step of setting the display content to be displayed in the first display section 25 by the patient 3 or the assistant and the display content to be displayed in the second display section 26 by the patient 3 or the assistant. The control then proceeds to step S2. Step S2 is a training step, which is the step in which the patient 3 conducts training while viewing the first display section 25 and the second display section 26. The control then proceeds to step S3. Step 3 is an end determination step. To change the display contents in the first display section 25 and the second display section 26, the control is caused to proceed to step S1. To stop conducting training, the rehabilitation is terminated.

The rehabilitation method will be described in detail in correspondence with the steps shown in FIG. 3 with reference to FIGS. 4 to 6. FIGS. 4 to 6 are figures corresponding to step S1 or the display content setting step and step S2 or the training step. FIG. 4 shows a case where the patient 3 has a paralyzed right hand and rehabilitates the right hand. In step S1, the patient 3 or the assistant selects the recorded image display selecting section 30 in the first input section 28 and the no-display selecting section 41 in the second input section 29. As a result, the first display section 25 displays recorded motion images formed of the left hand images 27a in which the patient 3 clenched and unclenched his/her left hand. The patient 3 can view live motion images of the right hand 3c in the second display section 6. The combination described above corresponds to a first combination.

In step S2 or the training step, the patient 3 clenches and unclenches his/her right hand while viewing the recorded motion images in the first display section 25. In this process, the patient 3 can simultaneously view the recorded motion images and the live motion images of the hand 3c of the patient 3. The recorded motion images are guidance motion images that the patient 3 emulates. The patient 3 moves the hand 3c by emulating the recorded motion images and checks the motion of the hand 3c by viewing the live motion images in the second display section 26. The method described above is referred to as rehabilitation therapy based on motion emulation. The method allows simultaneous observation of the guidance to be emulated and the motion of the hand 3c that emulates the guidance. The method therefore allows the patient 3 to simultaneously check a target of action and a result of the action and can hence improve the incentive of the patient 3. As a result, the patient 3 can efficiently conduct the training. The recorded motion images are preferably formed of a plurality motion images so that the patient 3 can change the hand clenching/unclenching speed in accordance with the degree of paralysis.

FIG. 5 shows a case where the patient 3 has a lost right hand and performs rehabilitation to remove phantom pain of the right hand. In step S1, the patient 3 or the assistant selects the no-display selecting section 34 in the first input section 28 and the left hand reversed skin color extraction selecting section 38 in the second input section 29. As a result, no motion images are displayed in the first display section 25, but the patient 3 can view the left hand 3c visible through the mirror sections 2a. The second display section 26 displays skin color reversed motion images of the left hand. The patient 3 can view left hand images 27b produced by reversing images of the hand 3c and an external background visible through the mirror sections 2a with the right hand images 27b and the external background superimposed on each other. The combination described above corresponds to a second combination.

In step S2 or the training step, the patient 3 conjures action of slowly clenching and unclenching his/her right hand in his/her mind while viewing the first display section 25 and the second display section 26. In this process, the patient 3 can view images 27b, which are mirror images produced by reversing images of the left hand, in the second display section 26. The patient 3 then conjures action of moving the right hand in his/her mind while viewing the moving images 27b in the second display section 26. The method described above is referred to as mirror therapy. In this method, the patient 3 can manipulate the speed and degree of the action of clenching and unclenching the reference hand. The patient 3 can therefore adjust the speed and degree of the action of clenching and unclenching the reference hand in such away that the patient 3 readily conjures the action in his/her mind. As a result, the patient 3 can efficiently conduct the training.

FIG. 6 shows a case where both hands or one of the hands of the patient 3 has been lost and the patient 3 performs rehabilitation to remove phantom pain of the lost hand(s). FIG. 6 instead shows a case where both hands or one of the hands of the patient 3 is paralyzed and the patient 3 performs rehabilitation to remove neuropathic pain of the paralyzed hand(s). In step S1, the patient 3 or the assistant selects the recorded image display selecting section 30 in the first input section 28 and the recorded image display selecting section 35 in the second input section 29. The patient 3 can therefore view recorded motion images formed of moving left hand images 27a in the first display section 25. The patient 3 can further view recorded motion images formed of moving right hand images 27b in the second display section 26. The recorded motion images are motion images in which the hands are repeatedly slowly clenched and unclenched. The combination described above corresponds to a third combination.

In step S2 or the training step, the patient 3 conjures action of slowly clenching and unclenching his/her hands in his/her mind while viewing the first display section 25 and the second display section 26. The method described above is referred to as a vision intervention method. In the method, the speed of the action of the reference hand images 27 and the degree of the action of clenching/unclenching the reference hand are set in accordance with the motion images. Therefore, the patient 3, when unaccustomed to the training, can be accustomed thereto by using the motion images as a reference. As a result, preparing motion images in which the action of the hand images 27 is performed at a variety of speeds and the hands are clenched and unclenched in a variety of degrees allows the patient 3 to readily conjure the clenching/unclenching action in his/her mind. The patient 3 can therefore efficiently conduct the training.

As described above, according to the present embodiment, the following advantageous effects are provided.

(1) According to the present embodiment, in a stroke-related training, the image section 24a displays recorded motion images and live motion images. The patient 3 moves a paralyzed body part by following the recorded motion images as guidance. The patient 3 can conduct training by checking the motion of the body part in the live motion images. In the phantom-pain-related training, the image section 24a displays reversed motion images and live motion images. In this process, the patient 3 conjures action of moving the lost hand 3c in his/her mind while viewing the reversed motion images. The patient 3 can conduct training by checking the motion of the hand 3c while viewing the live motion images and the reversed motion images. In the phantom-pain-related training, skin color reversed motion images are so displayed as to be superimposed on an external background. In the skin color reversed motion images, the background image in the captured images is removed, whereby the patient 3 can concentrate on the motion of the body part.

(2) According to the present embodiment, the display content setting section 16 can set display contents that are contents to be displayed in the first display section 25 and the second display section 26. Stroke-related training and phantom-pain-related training can therefore be conducted by setting the display content in each of the first display section 25 and the second display section 26 in accordance with the content of the training. The patient 3 can select one of live motion images, recorded motion images, reversed motion images, and skin color reversed motion images as motion images that allow the patient 3 to readily conduct training. The patient 3 can therefore select a combination of motion images that fits the patient's own training, whereby the training can be efficiently conducted.

(3) According to the present embodiment, the display content setting section 16 displays the dialog section 24b, which prompts input of display contents to be displayed in the image section 24a. The display content in the first display section 25 and the display content in the second display section 26 can be set in the single dialog section 24b. The display contents can therefore be set without switching the dialog section 24b, whereby the display contents in the head-mounted display 2 can be readily set.

(4) According to the present embodiment, the head-mounted display 2 is a light-transmissive head-mounted display. When the no-display selecting section 34 is selected in the first input section 28, the patient 3 can view the patient's own hand 3c visible through the mirror sections 2a in the first display section 25 because the mirror sections 2a of the head-mounted display 2 are light transmissive. Similarly, when the no-display selecting section 41 is selected in the second input section 29, the patient 3 can view the patient's own hand 3c visible through the mirror sections 2a in the second display section 26 because the mirror sections 2a of the head-mounted display 2 are light transmissive.

(5) According to the present embodiment, the skin color image extraction section 22 forms skin color reversed motion images. Since the background image in the skin color reversed motion images is removed, the patient 3 can concentrate on motion of the hand(s) 3c.

(6) According to the present embodiment, the first display section 25 displays recorded motion images in FIG. 4. In the second display section 26, the hand 3c of the patient 3 can be viewed through the head-mounted display 2. Therefore, the patient 3 can move the paralyzed hand 3c by following the recorded motion images as guidance and check the motion of the paralyzed hand 3c. The patient 3 can therefore simultaneously view the guidance and the action of the patient's own hand 3c, whereby the training can be efficiently conducted.

Second Embodiment

An embodiment of the rehabilitation assistance apparatus will next be described with reference to a block diagram showing the configuration of a rehabilitation assistance apparatus shown in FIG. 7. The present embodiment differs from the first embodiment in that the head-mounted display 2 is provided with a camera. The same points as those in the first embodiment will not be described.

Figure 7:
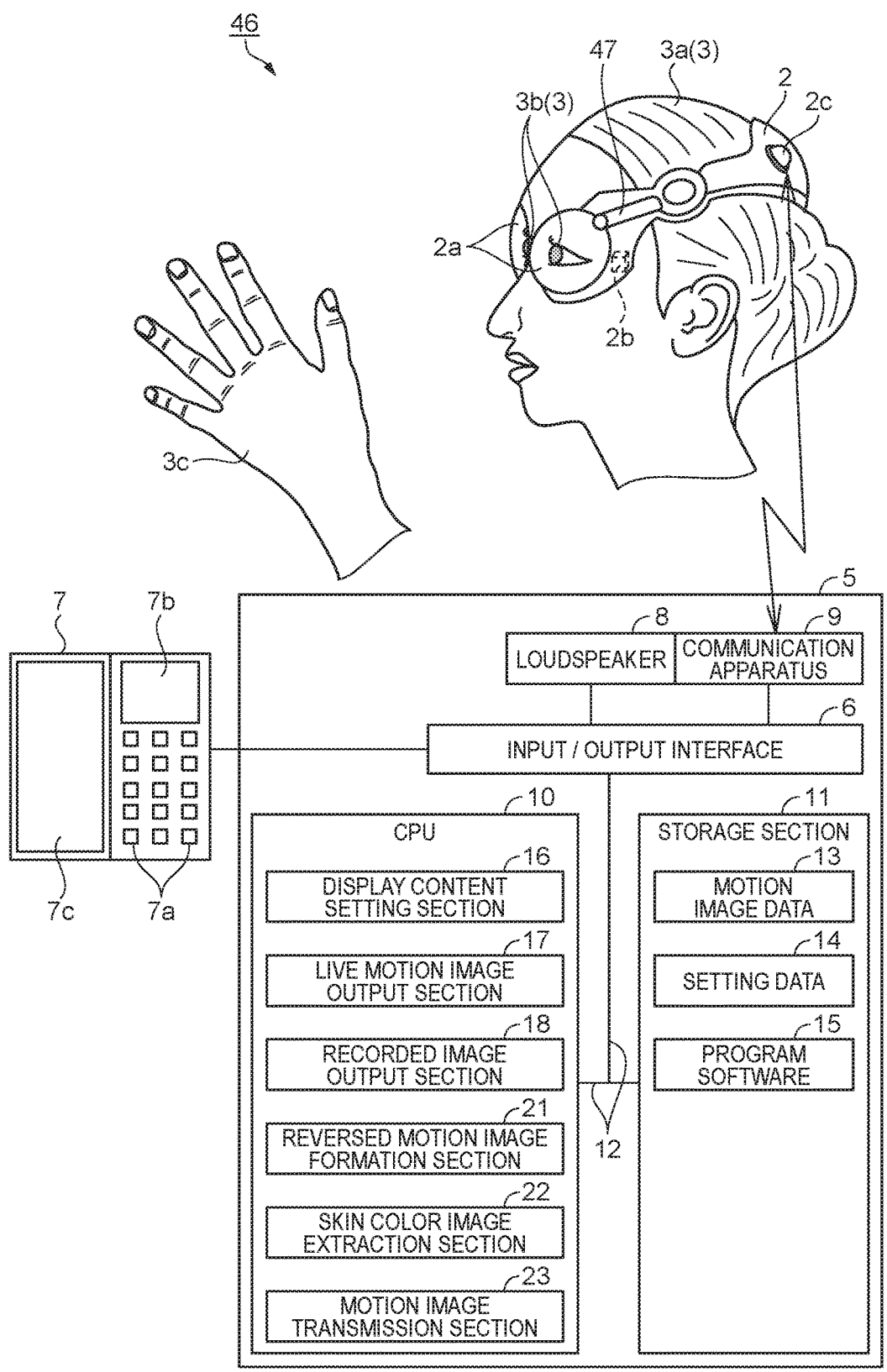
FIG. 7 is a block diagram showing the configuration of a rehabilitation assistance apparatus according to a second embodiment.

That is, in a rehabilitation assistance apparatus 46 of the present embodiment, the head-mounted display 2 is provided with a camera 47, as shown in FIG. 7. Live motion images captured with the camera 47 are transmitted by the communication section 2c to the communication apparatus 9. The camera 47 has the same function as that of the camera 4 in the first embodiment.

Since the head-mounted display 2 is provided with the camera 47, motion images captured with the camera 47 are synchronized with motion of the head 3a of the patient 3. The direction in which the camera 47 captures motion images has been so set as to coincide with the direction in which the line of sight of the patient 3 is oriented. Live motion images captured with the camera 47 are therefore the same as motion images of a scene viewed with the eyes of the patient 3. As a result, when the patient 3 moves the hand(s) 3c, the patient 3 can move the head 3a in synchronization with the motion of the hand(s) 3c, whereby the direction in which the camera 47 captures motion images can be adjusted.

Third Embodiment

Figure 8:
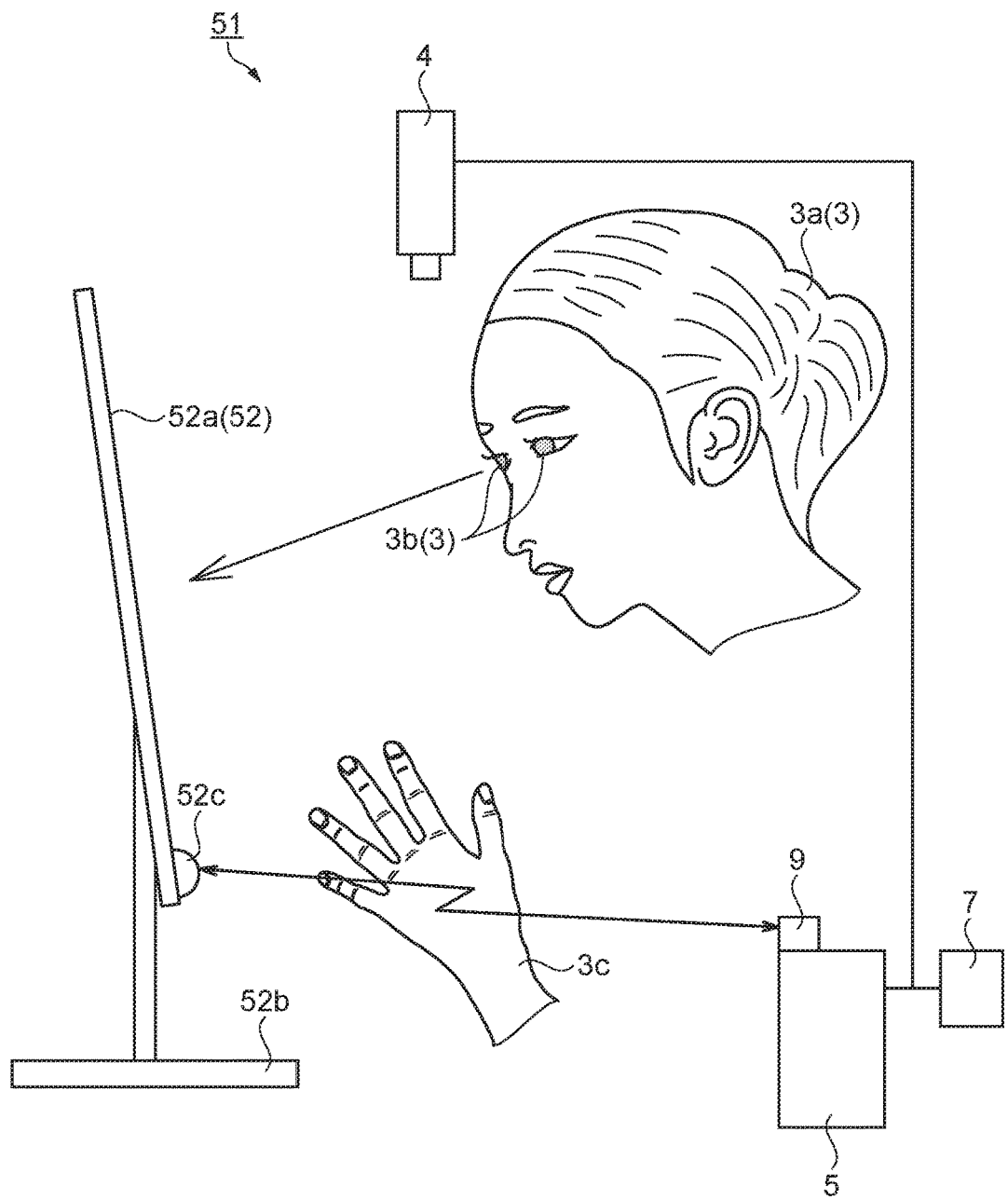
FIG. 8 is a block diagram showing the configuration of a rehabilitation assistance apparatus according to a third embodiment.
Figure 9:
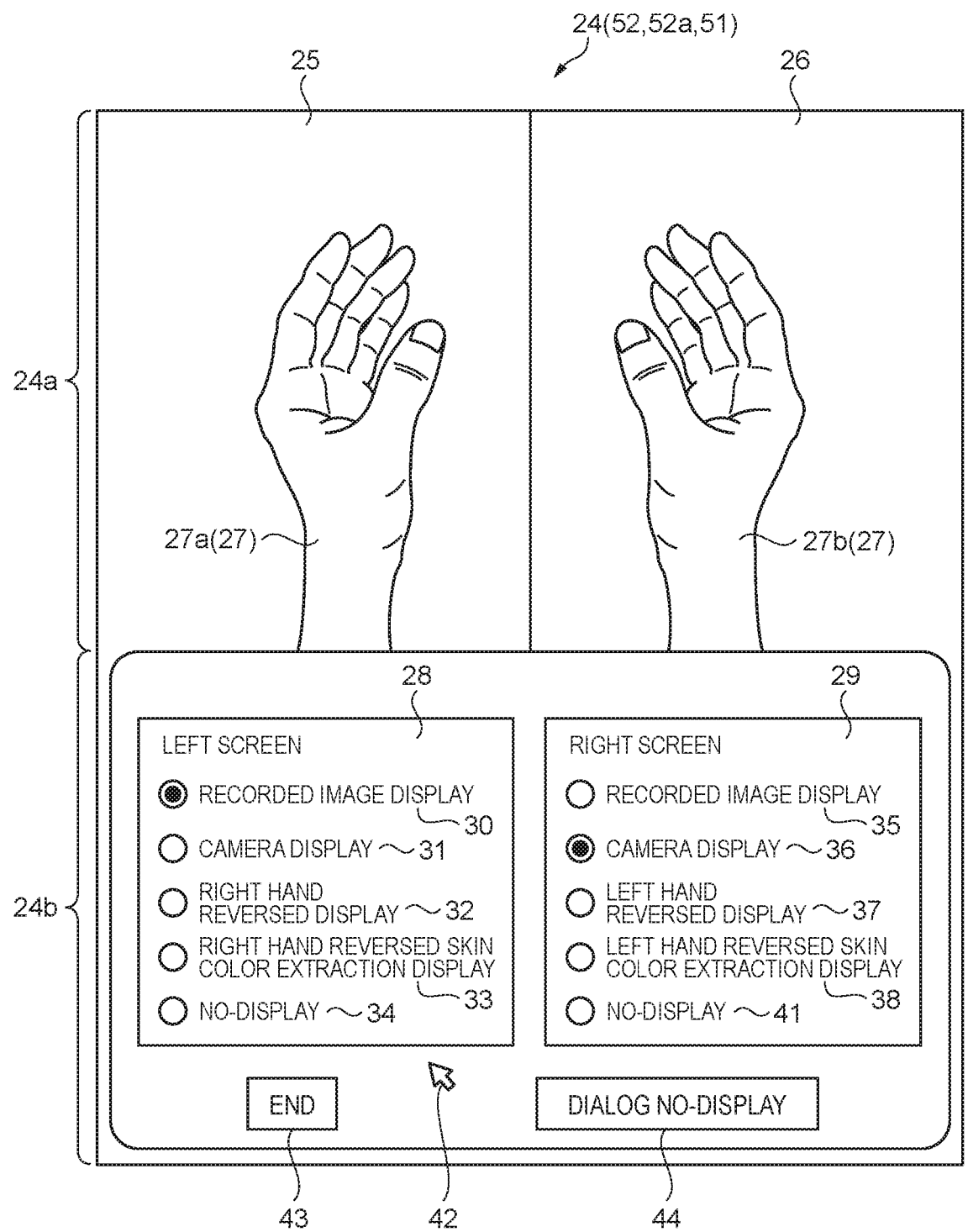
FIG. 9 is a diagrammatic view for describing the rehabilitation method.
Figure 10:
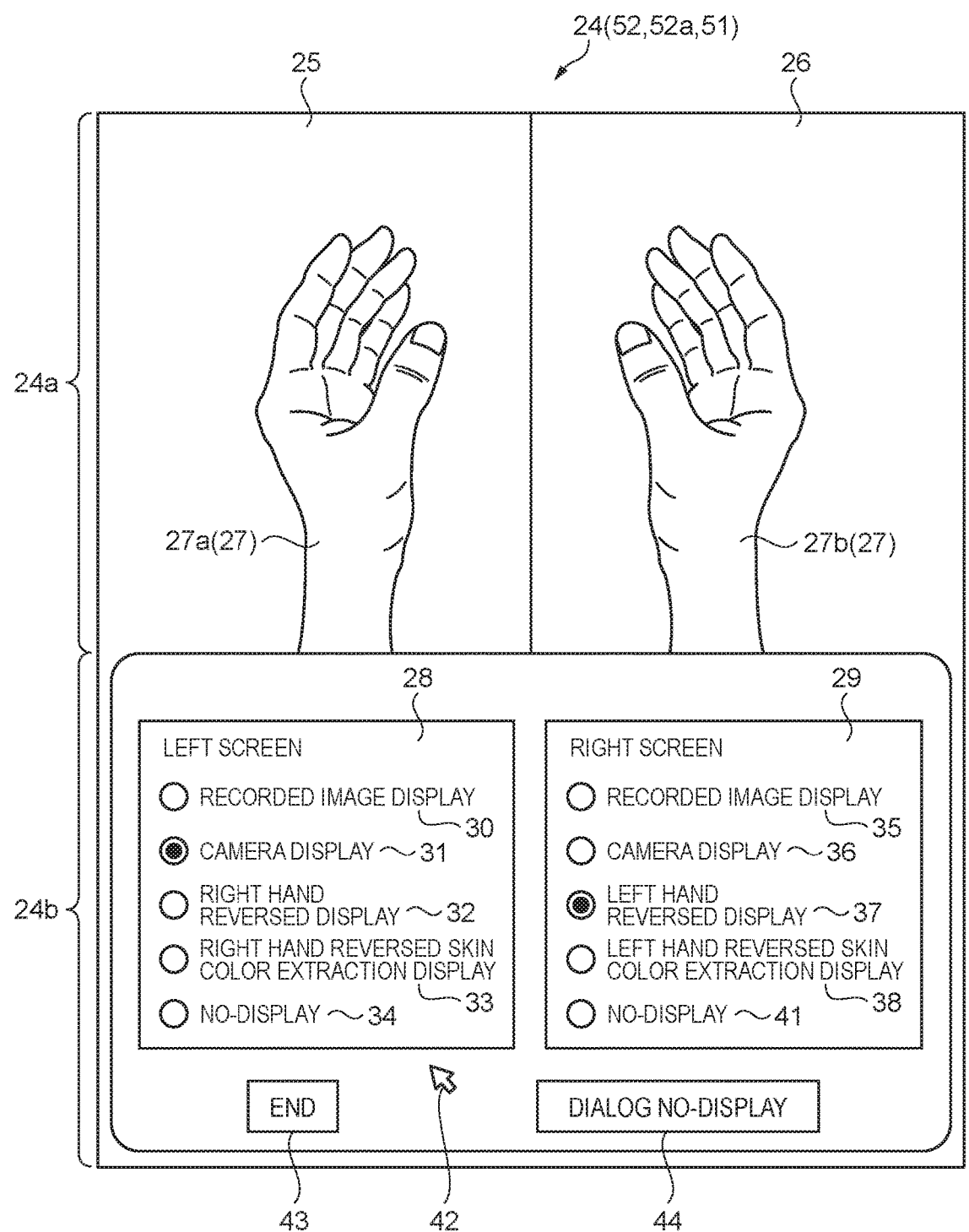
FIG. 10 is another diagrammatic view for describing the rehabilitation method.
Figure 11:
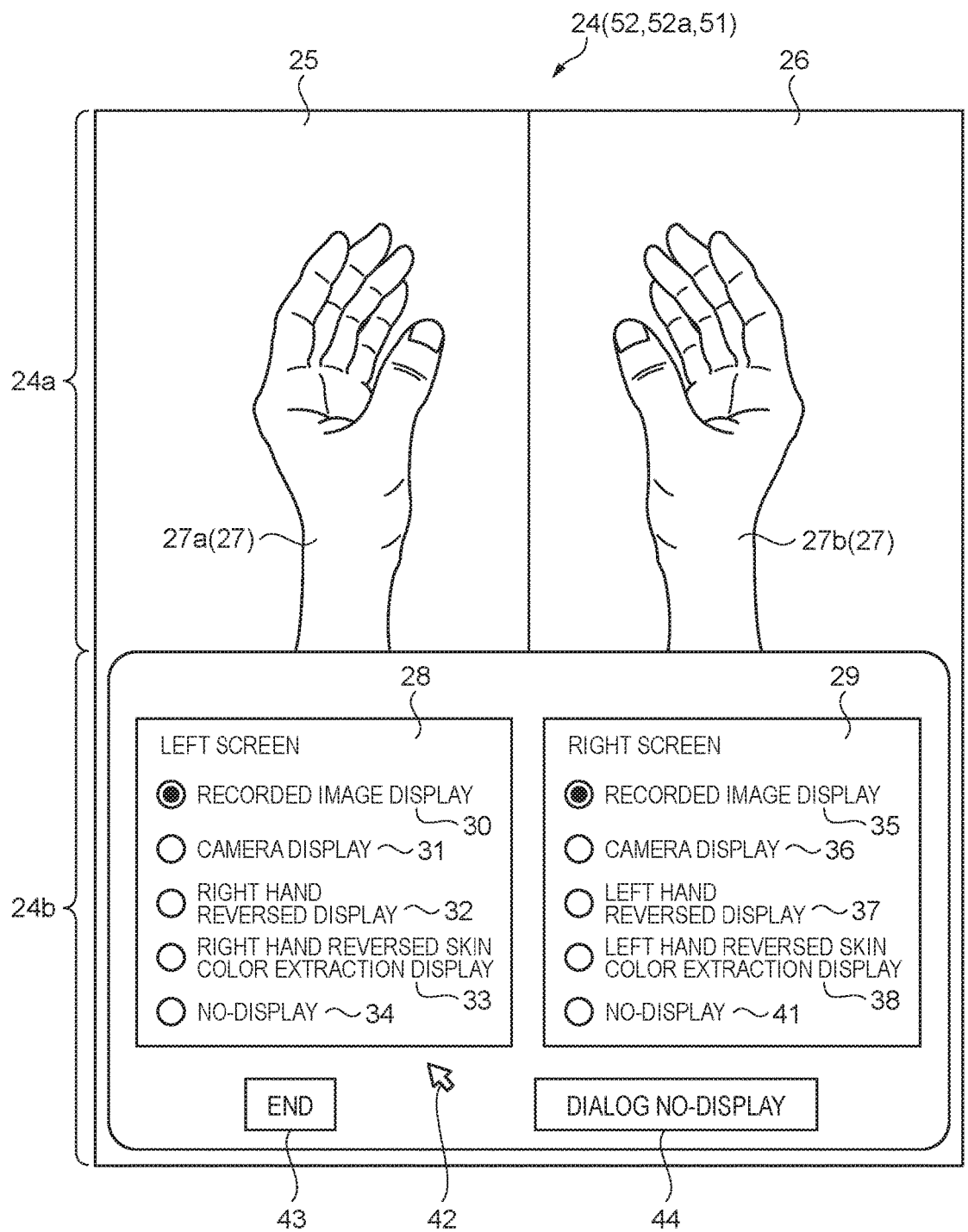
FIG. 11 is another diagrammatic view for describing the rehabilitation method.

An embodiment of the rehabilitation assistance apparatus will next be described with reference to FIGS. 8 to 11. FIG. 8 is a block diagram showing the configuration of the rehabilitation assistance apparatus. FIGS. 9 to 11 are diagrammatic views for describing a rehabilitation method. The present embodiment differs from the first embodiment in that the head-mounted display 2 is replaced with a panel-shaped display. The same points as those in the first embodiment will not be described.

That is, in the present embodiment, a rehabilitation assistance apparatus 51 includes a display 52, as shown in FIG. 8. The display 52 includes a display section 52a, a stand 52b, and a communication section 52c. The display 52 can be a liquid crystal display, an organic electroluminescence display, a plasma display, a field emission display, or any other display. The display 52 is preferably capable of color representation because color representation allows representation closer to the actual hand 3c than in monochrome representation.

The stand 52b is attached to the display 52 and allows the display section 52a to be inclined at a predetermined angle. The patient 3 can change the inclination angle of the display section 52a to a preferable angle for his/her training. The communication section 52c is attached to the display 52 and communicates with the communication apparatus 9 in the control apparatus 5. The communication section 52c receives motion image data from the control apparatus 5, and the display section 52a converts the received motion image data into motion images and displays them.

FIGS. 9 to 11 correspond to step S1 or the display content setting step and step S2 or the training step. FIG. 9 shows a case where the patient 3 has a paralyzed right hand and rehabilitates the right hand. In step S1, the patient 3 or the assistant selects the recorded image display selecting section 30 in the first input section 28 and the camera display selecting section 36 in the second input section 29. The first display section 25 therefore displays recorded motion images formed of left hand images 27a in which the left hand is clenched and unclenched. The second display section 26 displays live motion images formed of right hand images 27b captured with the camera 4. The combination described above corresponds to a first combination.

In step S2 or the training step, the patient 3 clenches and unclenches his/her right hand while viewing the recorded motion images in the first display section 25. In this process, the patient 3 can simultaneously view the recorded motion images and the live motion images of the hand 3c of the patient 3. The recorded motion images are guidance motion images that the patient 3 emulates. The patient 3 then moves the hand 3c by emulating the recorded motion images and checks the motion of the hand 3c by viewing the live motion images in the second display section 26. The method described above is referred to as rehabilitation therapy based on motion emulation. The method allows simultaneous observation of the guidance to be emulated and the motion of the hand 3c that emulates the guidance. The method therefore allows the patient 3 to simultaneously check a target of action and a result of the action and hence can improve the incentive of the patient 3. As a result, the patient 3 can efficiently conduct the training. The recorded motion images are preferably formed of a plurality motion images so that the patient 3 can change the hand clenching/unclenching speed in accordance with the degree of paralysis.

FIG. 10 shows a case where the patient 3 has a lost right hand and performs rehabilitation to remove phantom pain of the right hand. In step S1, the patient 3 or the assistant selects the camera display selecting section 31 in the first input section 28 and the left hand reversed display selecting section 37 in the second input section 29. As a result, the first display section 25 displays live motion images formed of images 27a of the left hand of the patient 3 captured with the camera 4. The second display section 26 displays reversed motion images of the left hand. The combination described above corresponds to a second combination.

In step S2 or the training step, the patient 3 slowly clenches and unclenches the patient's left hand while viewing the first display section 25 and the second display section 26. In this process, the patient 3 can view images 27b, which are mirror images produced by reversing images of the left hand, in the second display section 26. The patient 3 then conjures action of moving the right hand in his/her mind while viewing the moving image 27b in the second display section 26. The method described above is referred to as mirror therapy. In the method, the patient 3 can manipulate the speed of the action of the reference images 27b and the degree of the action of clenching and unclenching the patient's hand. The patient 3 can therefore adjust the speed and degree of the action of clenching and unclenching the patient's hand in such away that the patient 3 readily conjures the action in his/her mind. As a result, the patient 3 can efficiently conduct the training.

FIG. 11 shows a case where both hands or one of the hands of the patient 3 has been lost and the patient 3 performs rehabilitation to remove phantom pain of the lost hand(s). FIG. 11 instead shows a case where both hands or one of the hands of the patient 3 is paralyzed and the patient 3 performs rehabilitation to remove neuropathic pain of the paralyzed hand(s). In step S1, the patient 3 or the assistant selects the recorded image display selecting section 30 in the first input section 28 and the recorded image display selecting section 35 in the second input section 29. The patient 3 can therefore view recorded motion images formed of moving left hand images 27a in the first display section 25. The patient 3 can further view recorded motion images formed of moving right hand images 27b in the second display section 26. The recorded motion images are motion images in which the hands are repeatedly slowly clenched and unclenched. The combination described above corresponds to a third combination.

In step S2 or the training step, the patient 3 conjures action of slowly clenching and unclenching both the patient's hands in his/her mind while viewing the first display section 25 and the second display section 26. The method described above is referred to as a vision intervention method. In the method, the speed of action of the reference hand images 27 and the degree of action of clenching/unclenching the reference hand are set in accordance with the motion images. Therefore, the patient 3, when unaccustomed to the training, can be accustomed thereto by using the motion images as a reference. As a result, preparing motion images in which the action of the hand images 27 is performed at a variety of speeds and the hands are clenched and unclenched in a variety of degrees allows the patient 3 to readily conjure the clenching/unclenching action in his/her mind. The patient 3 can therefore efficiently conduct the training.

As described above, according to the present embodiment, the following advantageous effects are provided.

(1) According to the present embodiment, in FIG. 9, the patient 3 conducts training of the right hand paralyzed due, for example, to stroke. The display screen 24 displays live motion images and recorded motion images. The patient 3 moves the paralyzed hand 3*c* by following the recorded motion images as guidance. The patient 3 then checks the motion of the hand 3*c* by viewing the live motion images. The training is thus conducted. The patient 3 can therefore simultaneously view the guidance and the action of the patient's own hand 3*c*, whereby the training can be efficiently conducted.

(2) According to the present embodiment, in FIG. 10, the second display section 26 displays reversed motion images produced by reversing live motion images. The reversed motion images are motion images produced by reversing motion images of the hand 3*c* that the patient 3 can move. The patient can therefore conduct the training by using motion images showing motion that the patient can readily follow. As a result, the patient 3 can efficiently conduct the training.

Fourth Embodiment

Figure 12:
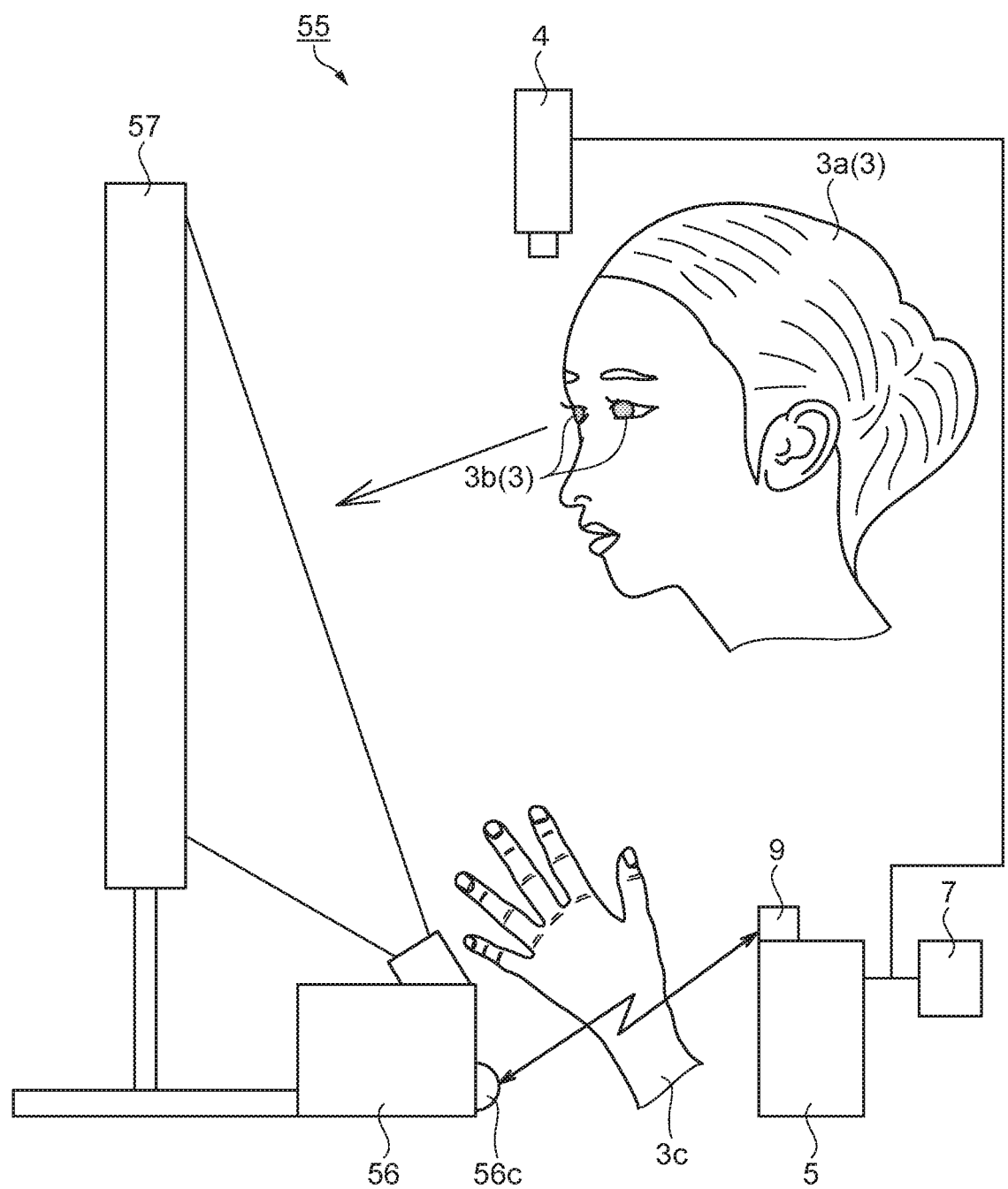
FIG. 12 is a block diagram showing the configuration of a rehabilitation assistance apparatus according to a fourth embodiment.

An embodiment of the rehabilitation assistance apparatus will next be described with reference to FIG. 12. FIG. 12 is a block diagram showing the configuration of the rehabilitation assistance apparatus. The present embodiment differs from the third embodiment in that the display 52 is replaced with a projector. The same points as those in the third embodiment will not be described.

That is, in the present embodiment, a rehabilitation assistance apparatus 55 includes a projector 56 and a screen 57, as shown in FIG. 12. The projector 56 includes a communication section 56*c*. The communication section 56*c* communicates with the communication apparatus 9 in the control apparatus 5. The communication section 56*c* receives motion image data from the control apparatus 5, and the projector 56 converts the received motion image data into motion images and projects them on the screen 57.

The patient 3 conducts training while viewing the screen 57. The motion images projected on the screen 57 can be larger than motion images displayed on the display 52. The patient 3 can therefore readily see motion images, whereby even a patient 3 who has poor eyesight can conduct training with no burden.

Embodiments of the invention are not limited to the embodiments described above, and a variety of changes and improvement can be made thereto by a person skilled in the art to the extent that the changes and improvements fall within the technical idea of the invention. Variations follow.

Variation 1

In the first embodiment described above, the case of the patient 3 who has a handicapped right hand is presented. The patient 3 who has a handicapped left hand can also use the rehabilitation assistance apparatus 1. This case can be handled by swapping the content displayed in the first display section 25 and the content displayed in the second display section 26 with each other.

Variation 2

In the first embodiment described above, a light-transmissive head-mounted display is used as the head-mounted display 2. A non-light-transmissive head-mounted display may instead be used as the head-mounted display 2. In this case, the camera display selecting section 31 is selected instead of the no-display selecting section 34 in the first input section 28, and the camera display selecting section 36 is selected instead of the no-display selecting section 41 in the second input section 29. Live motion images can thus be displayed on the display screen 24. Further, a transmissive mode and a non-transmissive mode may be switched from one to the other by providing the mirror sections 2*a* with a cover. One of the modes that allows the patient 3 to readily have a physical sensation as if the hand(s) 3*c* moved can be selected.

Variation 3

In the first embodiment described above, the patient 3 or the assistant selects the left hand reversed skin color extraction display selecting section 38 in the second input section 29 shown in FIG. 5. The left hand reversed display selecting section 37 may be selected instead of the left hand reversed skin color extraction display selecting section 38. Reversed motion images can be more readily formed than skin color reversed motion images, whereby reversed motion images can be formed quickly from captured motion images and displayed on the display screen 24.

Variation 4

In the first embodiment described above, the control apparatus 5 is connected to no external apparatus. The control apparatus 5 may be connected to a server via the communication apparatus 9 and a network. The setting data 14 used when the patient 3 starts the rehabilitation assistance apparatus 1 is stored in the server. When the patient 3 conduct training, the setting data 14 may be transferred from the server. When a plurality of rehabilitation assistance apparatus 1 are provided, the setting data 14 and the motion image data 13 stored last time can be used even when an apparatus different from the apparatus used lase time is used.

Variation 5

In the first embodiment described above, the rehabilitation assistance apparatus 1 is used to treat the hand(s) 3*c*. The rehabilitation assistance apparatus 1 may be used to treat a finger. Using motion images in which a finger moves allows the rehabilitation assistance apparatus 1 to provide the same advantageous effects as those in the first embodiment. Also in this case, the patient 3 or the assistant can use the input/output terminal 7 to set the display contents to be displayed on the display screen 24, and the patient 3 can view the thus set motion images. In addition, the rehabilitation assistance apparatus 1 can be used to treat a variety of other sites, such as an elbow, a knee, and the ankle of a foot. Variations 4 and 5 may be applied to the second to fourth embodiments described above.

Variation 6

In the third embodiment described above, the patient 3 or the assistant selects the left hand reversed display selecting section 37 in the second input section 29 shown in FIG. 10. The left hand reversed skin color extraction display selecting section 38 may be selected instead of the left hand reversed display selecting section 37. In this case, since the background is removed, the patient 3 is likely to be able to concentrate on the training.

In the first embodiment described above, the following three sections are provided: the live motion image output section 17; the recorded motion image output section 18; and the reversed motion image formation section 21. Instead, at least one of the three sections may be provided. Similarly, as the display content, at least one of live motion images, recorded motion images, reversed motion images, and skin color reversed motion images may be settable.

The entire disclosure of Japanese Patent Application No. 2015-033754 filed Feb. 24, 2015 is expressly incorporated by reference herein.

What is claimed is:

1. A rehabilitation display apparatus comprising:
a memory that includes computer-readable instructions and that stores recorded motion images;
a camera that outputs live motion images;
a motion image display having a first display section and a second display section; and
a processor that is configured to execute the computer-readable instructions to:
output the recorded motion images;
reverse the live motion images so as to form reversed motion images, the reversed motion images being line symmetric images of the live motion images;
extract images having a desired skin color from the live motion images so as to form extracted images;
reverse the extracted images so as to form skin color reversed motion images, the skin color reversed motion images being line symmetric images of the extracted images; and
set display contents that are displayed in the first display section and the second display section,
wherein the processor is configured to set one of the live motion images, the recorded motion images, the reversed motion images, and the skin color reversed motion images as the display contents in the first display section, and
the processor is configured to set the one of the live motion images, the recorded motion images, the reversed motion images, and the skin color reversed motion images or another one of the live motion images, the recorded motion images, the reversed motion images, and the skin color reversed motion images as the display contents in the second display section.

2. The rehabilitation display apparatus according to claim 1,
wherein the motion image display has a setting display section, the processor is configured to prompt input of the display contents, which are displayed in the first and second display sections, in the setting display section, and
the setting display section is formed of a single setting screen, and the processor is configured to display both the display contents displayed in the first display section and displayed in the second display section in the setting display section.

3. The rehabilitation display apparatus according to claim 1,
wherein the processor is configured to display the live motion images in one of the first display section and the second display section, and the processor is configured to display the recorded motion images in the other of the first display section and the second display section.

4. The rehabilitation display apparatus according to claim 1,
wherein the motion image display is a light-transmissive head-mounted display, and
when no motion images are displayed in the first display section and the second display section, a scene having passed through the motion image display is visible.

5. A rehabilitation display method for causing a processor to execute computer-readable instructions stored in a memory, the method comprising executing on the processor the steps of:

displaying motion images in a first display section and a second display section by using one of the following combinations:
a first combination in which recorded motion images are displayed in the first display section and live motion images are displayed in the second display section;
a second combination in which the live motion images are displayed in the first display section and reversed motion images produced by reversing the live motion images into line symmetric images are displayed in the second display section; and
a third combination in which the recorded motion images are displayed in the first display section and the second display section,
wherein in the second combination, skin color reversed motion images produced by extracting skin color images having a skin color from the live motion images and reversing the extracted skin color images into line symmetric images are displayed in the second display section.

6. The rehabilitation display method according to claim 5,
wherein the recorded motion images are produced by capturing an guidance action image.

7. The rehabilitation display method according to claim 5,
wherein the recorded motion images are produced by repeatedly capturing a clenched human hand image and a unclenched human hand image.

8. The rehabilitation display method according to claim 5,
wherein the reversed motion images are produced by capturing a normal body part image and by reversing the normal body part image into a line symmetric image of the normal body part image.

9. A non-transitory computer-readable medium for causing a computer to execute a process, comprising instructions thereon, that when executed on a processor, perform the steps of:
providing live motion images;
providing recorded motion images;
reversing the live motion images into line symmetric images to form reversed motion images;
extracting images having a skin color from the live motion images and reversing the extracted images into line symmetric images to form skin color reversed motion images; and
setting display contents that are contents to be displayed in a first display section and a second display section,
wherein the processor is configured to set one of the live motion images, the recorded motion images, the reversed motion images, and the skin color reversed motion images as the display contents.

10. The rehabilitation display apparatus according to claim 1,
wherein the recorded motion images are produced by capturing an guidance action image.

11. The rehabilitation display apparatus according to claim 1,
wherein the recorded motion images are produced by repeatedly capturing a clenched human hand image and a unclenched human hand image.

12. The rehabilitation display apparatus according to claim 1,
wherein the reversed motion images are produced by capturing a normal body part image and by reversing the normal body part image into a line symmetric image of the normal body part image.

13. The non-transitory computer-readable medium according to claim 9, wherein the recorded motion images are produced by capturing an guidance action image.

14. The non-transitory computer-readable medium according to claim 9,
wherein the recorded motion images are produced by repeatedly capturing a clenched human hand image and a unclenched human hand image.

15. The non-transitory computer-readable medium according to claim 9,
wherein the reversed motion images are produced by capturing a normal body part image and by reversing the normal body part image into a line symmetric image of the normal body part image.

16. A rehabilitation display method for causing a processor to execute computer-readable instructions stored in a memory, the method comprising executing on the processor the steps of:
displaying motion images in a first display section and a second display section by using one of the following combinations:
a first combination in which recorded motion images are displayed in the first display section and live motion images are displayed in the second display section;
a second combination in which the live motion images are displayed in the first display section and reversed motion images produced by reversing the live motion images into line symmetric images are displayed in the second display section; and
a third combination in which the recorded motion images are displayed in the first display section and the second display section,
wherein the recorded motion images are produced by repeatedly capturing a clenched human hand image and a unclenched human hand image.

17. The rehabilitation display method according to claim 16,
wherein in the second combination, skin color reversed motion images produced by extracting skin color images having a skin color from the live motion images and reversing the extracted skin color images into line symmetric images are displayed in the second display section.

\* \* \* \* \*